United States Patent [19]
Zeiss

[11] Patent Number: 5,633,385
[45] Date of Patent: May 27, 1997

[54] OPTICALLY ACTIVE ω-HALO-2-AMINO-ALKANECARBOXYLIC ACID DERIVATIVES, PROCESS FOR THE PREPARATION THEREOF AND THEIR USE FOR THE PREPARATION OF OPTICALLY ACTIVE PHOSPHORUS-CONTAINING α-AMINO ACIDS

[75] Inventor: Hans-Joachim Zeiss, Sulzbach/Taunus, Germany

[73] Assignee: Hoechst Schering AgrEvo GmbH, Berlin, Germany

[21] Appl. No.: 465,433

[22] Filed: Jun. 5, 1995

Related U.S. Application Data

[62] Division of Ser. No. 337,322, Nov. 10, 1994, abandoned, which is a continuation of Ser. No. 924,342, Jul. 31, 1992.

[30] Foreign Application Priority Data

Aug. 3, 1991 [DE] Germany .................. 41 25 753.7

[51] Int. Cl.$^6$ .................................................. C07D 263/06
[52] U.S. Cl. ........................................................ 548/228
[58] Field of Search .......................... 548/228; 514/376

[56] References Cited

U.S. PATENT DOCUMENTS 4,012,412  3/1977  Yamanaka et al. .................. 548/228

FOREIGN PATENT DOCUMENTS

| | | |
|---|---|---|
| 0346658 | 12/1989 | European Pat. Off. . |
| 89-4012 | 12/1989 | South Africa . |
| 2011416 | 7/1979 | United Kingdom . |

OTHER PUBLICATIONS

Barton, J. Chem. Soc. Chem. Comm., 1984, pp. 1298–1299.
Goldschmidt et al., Liebig, Annalen der Chemie, vol. 649 (1961), pp. 1–13.
Kochi et al., J. Am. Chem. Soc. 87 (1965), pp. 1508–1514.
Scholz et al., Synthesis Stuttgart, 1989, pp. 542–547.
Baldwin, Tetrahedron 42, (1986), pp. 6551–6554.
Arshady et al., J. Chem. Soc. Chem. Comm., 1989, pp. 423–425.
Merck Index, 10th Ed. (1983) p. ONR4,61.
Tamaru, Chem. Abstract vol. 111, entry 56578x (1989).
Derek, H.R. Barton et al., "Manipulation of the carboxyl groups of α–amino–acids and peptides using radical chemistry based on esters of N–hydroxy–2–thiopyridone", Tetrahedron, vol. 44, No. 17, pp. 5479–5486 (1988).
Barrie W. Bycroft et al., "A Chiral synthesis of trans–carbapenam–3–carboxylic acid and the assignment of (3S,5S) configuration to the corresponding product from Serratia and Erwinia Species", J. Chem. Soc. Comun., pp. 423–425 (1989).
Nobuto Minowa et al., "Asymmetric synthesis of (+)–phosphinothricin and related compounds by he Michael addition of glycine Schiff bases to vinyl compounds", Bull.. Chem. Soc. Jpn. vol. 60, pp. 1761–1766 (1987).
J. Kollonitsch et al., JACS 86 (1964), pp. 1857 and 1858.
J. Kollonitsch et al., JACS 88 (1966), pp. 3624–3626.
Band et al., JCS Chem. Comm. (1966), pp. 544–545.
Tamaru et al., Angew. Chem. 101Int. Eng. Ed. vol. 28 (1989), No. 3, pp. 358–360.
Tamaru et al., Angew. Chem. Int. Eng. Ed. vol. 28 (1989), pp. 351–353.
CA102: 149731w Reductive . . . peptides. Barton et al., p. 658, 1985.
CA110: 154868r Manipulation . . . –2–thiopyridine. Barton et al., p. 780,, 1989.
CA111: 56578x Copper (I)–assisted . . . β–amino acids. Tamaru et al., 1989.

*Primary Examiner*—Joseph McKane
*Attorney, Agent, or Firm*—Curtis, Morris & Safford, P.C.

[57] ABSTRACT

Optically active, cyclic (2S)- and (2R)-ω-halo-2-aminoalkanecarboxylic acid derivatives of the formula I and mixtures thereof,

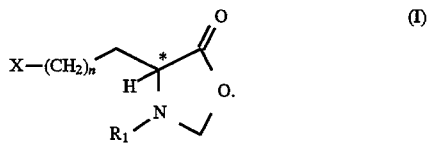

4 Claims, No Drawings

OPTICALLY ACTIVE ω-HALO-2-AMINO-ALKANECARBOXYLIC ACID DERIVATIVES, PROCESS FOR THE PREPARATION THEREOF AND THEIR USE FOR THE PREPARATION OF OPTICALLY ACTIVE PHOSPHORUS-CONTAINING α-AMINO ACIDS

This application is a division of application Ser. No. 08/337,322, filed on Nov. 10, 1994, now abandoned, which is a continuation of Ser. No. 07/924,342, filed on Jul. 31, 1992, now pending.

DESCRIPTION

Optically active ω-halo-2-aminoalkanecarboxylic acid derivatives, process for the preparation thereof and their use for the preparation of optically active phosphorus-containing α-amino acids The invention relates to optically active, cyclic (2S)- and (2R)-ω-halo-2-aminoalkanecarboxylic acid derivatives of the formula I and mixtures thereof,

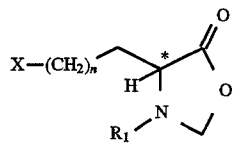

in which $R_1$ is $(C_1-C_6)$alkyl which is unsubstituted or is substituted by one or more radicals selected from the group comprising hydroxyl, $(C_1-C_4)$alkoxy, $[(C_1-C_4)$alkyl] carbonyl and $[(C_1-C_4)$alkoxy]carbonyl; or is $(C_2-C_6)$ alkenyl, $(C_2-C_6)$alkynyl or a group of the formula $R_2$—CO— or $R_3$—$S_2$—, $R_2$ is $(C_1-C_{11})$alkyl, $(C_6-C_{13})$aryl or substituted $(C_6-C_{13})$ aryl, $(C_1-C_6)$alkoxy, which is unsubstituted or substituted by one or more radicals, preferably a radical selected from the group comprising $(C_6-C_{13})$aryl and substituted $(C_6-C_{13})$aryl, $R_3$ is $(C_1-C_4)$alkyl, phenyl or substituted phenyl, X is halogen, preferably chlorine, bromine or iodine, and n is zero or one, in particular one, which are suitable as starting materials for the preparation of a multiplicity of biologically active substances.

In the formula (I), the carbon chains in the radicals mentioned, such as unsubstituted or substituted alkyl, alkoxy and other radicals, can each be straight-chain or branched. Alkyl radicals, including those in combined definitions such as alkoxy, haloalkyl, etc. are for example methyl, ethyl, n- or i-propyl, n-, i-, t- or 2-butyl etc. alkenyl and alkynyl radicals are the possible unsaturated radicals corresponding to the alkyl radicals, such as for example 2-propenyl, 2- or 3-butenyl, 2-propynyl, or 2- or 3-butynyl. Halogen is fluorine, chlorine, bromine or iodine. Aryl is an aromatic radical, for example phenyl, naphthyl or fluorenyl, preferably phenyl. Substituted aryl or phenyl is for example aryl or phenyl which is substituted by one or more, preferably one to three, radicals selected from the group comprising halogen, $(C_1-C_4)$alkyl, $(C_1-C_4)$alkoxy, $(C_1-C_4)$ thioalkyl, $[(C_1-C_4)$alkyl]carbonyl, $[(C_1-C_4)$alkoxy] carbonyl, $[(C_1-C_4)$alkyl]carbonyloxy, carboxamide, $[(C_1-C_4)$alkyl]carbonylamino, $[(C_1-C_4)$alkyl] aminocarbonyl, di-$[(C_1-C_4)$alkyl]aminocarbonyl and nitro. Substituted aryl is preferably phenyl which is substituted by one or more, preferably one to three, radicals selected from the group comprising halogen, $(C_1-C_4)$alkyl, $(C_1-C_4)$alkoxy and nitro.

Examples of radicals having carbonyl groups mentioned under $R_1$ are acetyl, methoxycarbonyl, ethoxycarbonyl, tert-butoxycarbonyl, benzyloxycarbonyl, fluorenylmethoxycarbonyl and naphthylmethoxycarbonyl.

Some compounds of the formula (I) can, in addition to the indicated center of asymmetry, contain one or more asymmetric carbon atoms or double bonds, which are not given separately in the formula (I). However, the possible stereoisomers defined by their specific spatial form, such as enantiomers, diastereomers, Z- and E- isomers, are all included by the formula (I) and can, if required, be obtained by conventional methods from mixtures of the stereoisomers or can alternatively be prepared by stereoselective reactions in combination with the use of stereochemically pure starting materials.

Preferred compounds of the formula I mentioned are those in which $R_1$ is 1-hydroxy$(C_1-C_6)$alkyl, methanesulfonyl, benzenesulfonyl, o-, m- or p-toluenesulfonyl or a group of the formula $R_2$—CO—, $R_2$ is $(C_1-C_{11})$alkyl, $(C_6-C_{12})$aryl or substituted $(C_6-C_{12})$ aryl, $(C_1-C_4)$alkoxy, which is unsubstituted or substituted by one or more radicals, preferably a radical selected from the group comprising phenyl and substituted phenyl, X is chlorine, bromine or iodine and n is zero or one.

Particular preference is given to compounds of the formula I in which $R_1$ is 1-hydroxy$(C_1-C_4)$alkyl, methanesulfonyl, benzenesulfonyl, p-toluenesulfonyl, methoxycarbonyl, ethoxycarbonyl, tert-butoxycarbonyl or benzyloxycarbonyl.

Particular preference is also given to those compounds of the formula I which have a combination of the abovementioned preferred characteristics.

The optically active compounds of the formula include the (2S) or (2R) compounds of the formulae $I_S$ and $I_R$

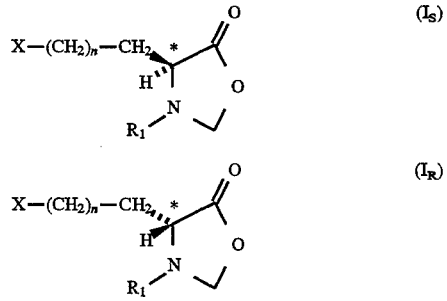

in which $R_1$, X and n have the abovementioned meaning.

Particular preference is given to optically active (2S) compounds of the formula Is or mixtures of the isomers Is and $I_R$ having a content of more than 80%, preferably more than 90%, of the compound of the formula $I_S$. Numerous syntheses of biologically active substances are already known via predominantly acyclic ω-halo-2-aminoalkanecarboxylic acid derivatives. Such compounds are used for example in the synthesis of cystathionine-containing peptides (Coll. Czech. Chem. Comm. 1967, 32, 485), in the synthesis of optically active azetidinecarboxylic acid (Chem. Lett. 1973, 5), in the preparation of modified t-RNA (Chem. Ber. 1976, 109, 82), in the synthesis of sweeteners (J. Agric. Food Chem. 1982, 30, 676) and principally in the synthesis of substituted amino acids (Tetrahedron 1985, 41, 1833) such as for example L-canaline (Lieb. Ann. Chem, 1986, 287), L-selenomethtonine (Tetrahedron 1986, 4983) or aminocyclopropanecarboxylic acid (Synthesis 1987, 298). In addition, they can be used for the synthesis of the microbial inhibitor discadenine (Synthesis 1988, 240) and for the preparation of antibiotics of the nocardicin group (J. Am. Chem. Soc. 1990, 112, 760).

However, cyclic derivatives of ω-halo-2-aminoalkanecarboxylic acids of the abovementioned formula I have not hitherto been used. In J. Chem. Soc. Chem. Comm. 1984, 1298, the preparation of a compound of the formula I is described in which $R_1$=benzyloxycarbonyl, X=Br and n=1, the starting material used being the not readily available or expensive N-hydroxypyridine-2-thione. The optical yield of the compound described (formula I, Rx=benzyloxycarbonyl, X=Br, n=1) is to be considered as very poor because of the optical rotation obtained. The chemical yield obtained in this case of 73% of theory is likewise too low for industrial exploitation.

It has now been found that the cyclic compounds of the formula I are further valuable synthons, and are particularly highly suitable for the preparation of certain optically active phosphorus-containing α-amino acids defined in more detail further below.

The invention therefore relates to optically active, cyclic ω-halo-2-aminoalkanecarboxylic acid derivatives of the formula I mentioned or mixtures thereof in which $R_1$, X and n have the meaning given under formula I, except for the known compound of the formula I in which $R_1$=benzyloxycarbonyl, X=Br and n=1.

In order to exploit to the full the synthetic potential of the optically active, cyclic ω-halo-2-aminoalkane-carboxylic acid derivatives of the formula I, a process is required which starts with cheap, readily available starting materials and which gives the desired compounds of the formula I in high chemical and optical yield.

The invention further relates to a process of this type for the enantioselective synthesis of the novel and known optically active ω-halo-2-aminoalkanecarboxylic acid derivatives of the formula I mentioned in which $R_1$, X and n have the meaning given under formula I, which comprises a) in the case of the compounds of the formula $I_S$ mentioned, reacting an optically active diacyl peroxide of the formula $II_S$ (see equation 1) in which $R_1$ and n have the same meaning as in formula I Equation 1

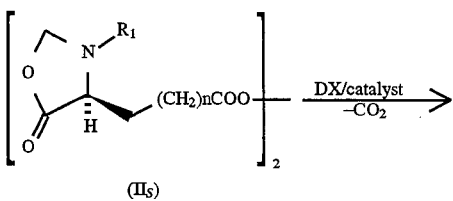

($II_S$)

($I_S$)

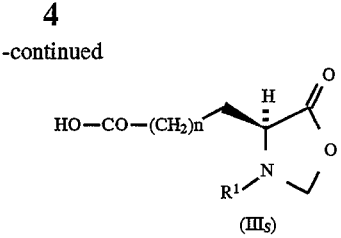

($III_S$)

in a nitrile group-containing solvent in the presence of a copper-containing catalyst with a halogenation agent DX and isolating the compound of the formula $I_X$ from the resulting mixture of the compounds $I_S$ and $III_S$ (see equation 1) or b) in the case of the compounds of the formula $I_R$ mentioned or mixtures of the compounds of the formulae $I_R$ and $I_S$, using an optically active diacyl peroxide $II_R$, which corresponds to the compound of the formula $II_S$ mentioned under a), but which instead of the (S) configuration at the respective asymmetric carbon atom has the (R) configuration, or a corresponding mixture of the diacyl peroxides $II_R$ and $II_S$, and reacting them as under a) and isolating the compound of the formula $I_R$ or the mixture of the compounds of the formulae $I_R$ and $I_S$.

The reaction occurring in the conversion formally corresponds to the Hunsdiecker degradation and has hitherto been described only for defunctionalized, diacyl peroxides (Lieb. Ann. Chem. 1961, 649, 1; J. Am. Chem. Soc. 1965, 87, 1508).

The reaction of the acyl peroxides of the formula $II_S$ or $II_R$ is preferably carried out in a temperature range from −30° to +100° C., in particular −5° to +80° C., but in each case preferably at a temperature which is below the decomposition temperature of the respective compound. The temperature of the uncatalyzed, thermal decomposition can be determined by known processes, such as for example by differential thermal analysis. In order to avoid the danger of spontaneous decomposition, it is moreover advisable to test the sensitivity to impact of each starting material used.

The chief solvents used are organic nitriles. Examples of these are aliphatic mono- or dinitriles, such as acetonitrile, propionitrile and also octanedinitrile, or aromatic nitriles, such as benzonitrile and substituted benzonitriles.

Mixtures of nitriles and other solvents, for example carboxylic acids, can likewise be used, in order to increase the solubility of the copper catalyst used in each case. Examples of carboxylic acids which may be used are acetic acid, chloroacetic acid or propionic acid.

Suitable halogenation agents DX are for example the elementary halogens, such as chlorine, bromine and iodine, phosphorus(V) halides or copper halides.

Suitable catalysts are copper compounds in all valency states, for example copper(I) oxide and copper halides such as copper(I) bromide, copper(II) bromide and copper(I) iodide.

Thus in the case where X=Br, elementary bromine or phosphorus(V) bromide for example act as the halogenation agent DX, in the case where X=Cl, phosphorus(V) chloride for example acts as the halogenation agent DX, the catalyst used in these cases being preferably copper(I) oxide.

If the elementary halogens are used, the catalysts used can be corresponding copper halides, for example the combination $Br_2/CuBr_2$.

In the case X=Br and X=iodine, a particularly preferred variant of the process according to the invention is to use copper halides as halogenation agent and simultaneously as catalyst. Thus for the preparation of compounds of the formula I, copper(I) bromide, copper(II) bromide or copper (I) iodide can advantageously be used. Alternatively for the case X=Cl, copper(I) chloride and copper(II) chloride can be used.

The amount of catalyst used can be varied within wide ranges, but when copper halides are used it should be ensured that at least the stoichiometrically required quantity of halide is present in the system.

The duration of reaction is dependent on the reaction temperature and is between 0.5 and 30 hours.

All reactions are expediently carried out With exclusion of oxygen, that is under a protective gas atmosphere or in vacuo. Protective gases which can be used are for example nitrogen or argon.

The isolation of the compound of the formula I from the reaction mixture can be carried out by conventional methods, such as for example by acid/base separation or by chromatography of the mixture which contains the compounds of formulae I ($I_S$ or $I_R$) and III ($III_S$ or $III_R$).

To separate the compounds of the formulae $I_S$ and $III_R$ (or $I_R$ and $III_R$), the solvent used in the reaction is for example completely distilled off and the residue is taken up in a solvent immiscible with water, such as for example toluene, xylene, dichlorobenzene, ethyl acetate or dichloromethane or mixtures of these solvents. To separate off the carboxylic acid component III, the organic phase is then washed with dilute aqueous sodium hydroxide solution, dilute hydrogen carbonate solution, hydrogen phosphate buffer solution or with another basic solution, the pH preferably not exceeding 8.5. The crude compound of the formula I obtained in this manner in the organic phase can be isolated by distilling off the solvent, generally under reduced pressure, and, if desired, can be further purified by known methods such recrystallization or chromatography.

After acidification of the alkaline, aqueous phase, the carboxylic acid component of the formula III can be extracted from this by means of an organic solvent and isolated in a conventional manner. If desired, the recovered carboxylic acid component can be reused for the preparation of the diacyl peroxide of the formula II required as the starting material.

Diacyl peroxides of the formula II are novel and are therefore likewise subject matter of the present invention.

The diacyl peroxides II ($II_S$ or $II_R$) required as starting material can be obtained from the carboxylic acid chlorides of the formula IIIa ($IIIa_S$ or $IIIa_R$) by reaction with hydrogen peroxide (see equation 2, only reproduced for the S forms).

Equation 2

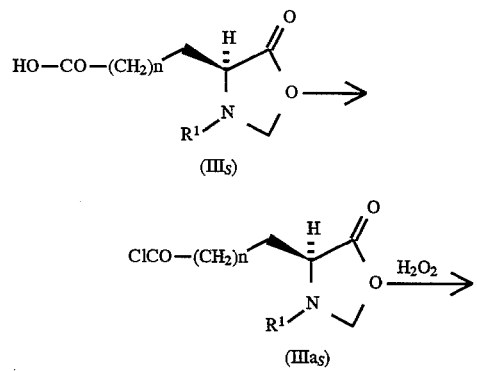

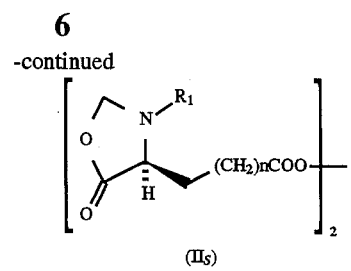

The reaction with hydrogen peroxide is carried out for example in an organic or aqueous/organic solvent in the presence of a base. Suitable solvents for this are organic solvents selected from the group comprising aliphatic or aromatic, unhalogenated or halogenated hydrocarbons, ethers such as diethyl ether or tetrahydrofuran and esters such as ethyl acetate. Suitable bases are inorganic and organic bases, for example organic bases selected from the group comprising the tertiary organic amines such as pyridine, triethylamine and 1,8-diazabicyclo[5.4.0]undec-7-ene. The reaction temperature is generally −20° to +20°, preferably 0° to 10° C.

The preparation of the carboxylic acid chlorides of the formula IIIa from the free carboxylic acids of the formula III and also the preparation of the carboxylic acids of the formula III can be carried out according to, or by analogy with, known methods (Synthesis 1989, 542; Tetrahedron 1986, 42, 6551; Rec. Tray. Chim. 1975, 94, 182; Coll. Czech. Chem. Comm. 1963, 28, 2941).

The compounds of the formula III, in particular $III_S$, can be obtained in a known manner from aspattic acid and glutamic acid, in particular L-aspartic acid or L-glutamic acid (references: Chem. Pharm. Bull. 1969, 1679; Synthesis 1989, 542; Tetrahedron 1986, 6551; J. Chem. Soc. Chem. Comm. 1989, 423; Chemische Berichte 95, 1009 (1962)). It is a particular advantage of the preparation processes according to the invention described above and below that the amino acids L-aspartic acid and L-glutamic acid which are cheap and available in large quantities can be used as starting materials for the preparation of optically active synthons and active substances.

The invention further relates to the use of the compounds obtained in this manner of the formula I for the synthesis of derivatives of optically active phosphorus-containing α-amino acids of the formula V. The process according to the invention for the preparation of the compounds of the formula V is a type of Arbusov reaction and is illustrated in equation 3 with the example of the compounds of the formulae $I_S$ and $V_S$ having the (2S) configuration.

Equation 3

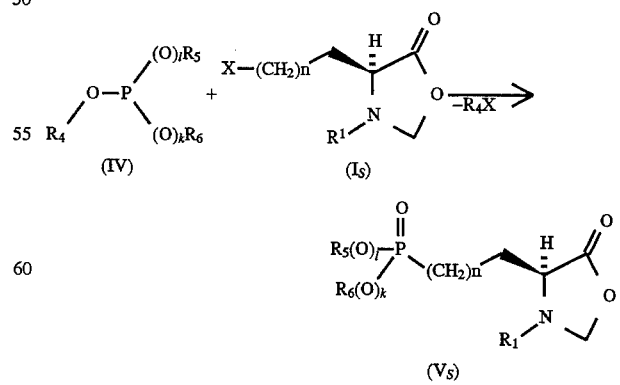

In the formulae I, IV and V (respectively $I_S$, $I_R$, $IV_S$, $IV_R$, $V_S$, $V_R$)

$R_4$ is trialkylsilyl, $(C_1-C_8)$alkyl, $(C_3-C_8)$cycloalkyl, $(C_6-C_{13})$aryl or substituted $(C_6-C_{13})$ aryl, $R_5$, $R_6$ are, independently of each other, $(C_1-C_8)$alkyl, $(C_3-C_8)$cycloalkyl, $(C_6-C_{13})$ aryl or substituted $(C_6-C_{13})$, k is zero or one, preferably one and l is zero or one, preferably zero;

$R_1$, X and n have the meanings already mentioned further above.

Trialkylsilyl in the above definition of $R_4$ is taken to mean preferably tri($C_1-C_6$-alkyl)silyl, in particular trimethylsilyl, triethylsilyl, tributylsilyl and tertbutyldimethylsilyl.

Some of the cyclic derivatives of optically active, phosphorus-containing α-amino acids of the formula V obtainable by the process according to the invention (cf. equation 3) are described in German Offenlegungsschrift 3,817,956 (ZA 89/4012) and can be used as intermediates for the preparation of the free amino acids of the formula VI and their peptides (cf. equation 4). The compounds of the formula VI and numerous peptides thereof have herbicidal, fungicidal and antiviral properties (see Bull. Chem. Soc. Japan 1987, 60, 1761; German Offenlegungsschrift 2,856, 260 (GB-A-2,011,416); Sci. Rep. Meiji Seika Kaisha 1973, 13, 34; Biochem. 1964, 3,991).

Equation 4

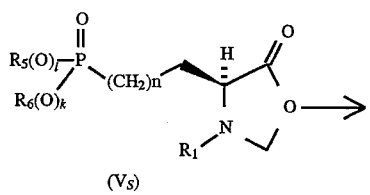

(V$_S$)

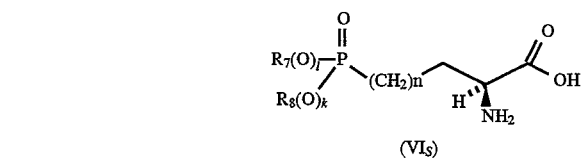

(VI$_S$)

In the formula VI (respectively VI$_S$ or VI$_R$)

$R_7=R_5$ or, if l=1 and k=1, $R_5$ or hydrogen and $R_8=R_6$ or, if l=1 and k=1, $R_e$ or hydrogen, and $R_1$, n, k and l have the meanings already mentioned under formula I and formula IV.

In the case of the compounds of the formula (VI) or (VI$_S$), respectively, particular importance is attached to the amino acid 4-[hydroxy(methyl)phosphinoyl]homoalanine (VI) or (2S)-4-[hydroxy(methyl)phosphinoyl]homoalanine (VI$_S$), respectively, the latter termed in brief hereafter L-phosphinothricin or L-PTC for short (see formula below), which in the free form or in the form of its salts is the active substance of the herbicide glufosinate (D,L-PTC) (cf. "The Pesticide Manual", 9th edition 1991, 458):

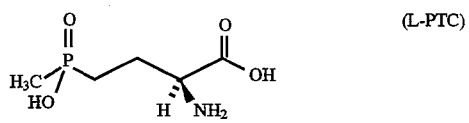

(L-PTC)

The process according to the invention thus allows the preparation of L-phosphinothricin and other phosphorus-containing L-amino acids starting from the easily available amino acids L-glutamic acid or L-aspartic acid.

The reaction of compounds of the formula I with phosphorous, phosphonous or phosphinous acid derivatives of the formula IV leads, as illustrated in equation 3, in an Arbusov reaction (Chem. Rev. 1981, 81, 415), to the cyclic derivatives of optically active, phosphorus-containing α-amino acids V, which, as described in German Offenlegungsschrift 3,817,956 (ZA 89/4012), can be further derivatized. If the phosphorus component used is for example diesters of methanephosphonous acid, compounds of the formula Va$_S$ are obtained by reaction with a compound of the formula I$_S$, which compounds of the formula Va$_S$ can be converted in a known manner into L-PTC (German Offenlegungsschrift 3,817,956 (ZA 89/4012)).

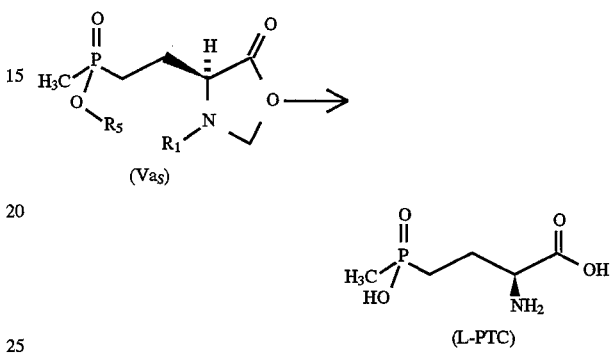

Starting from L-glutamic acid, L-phosphinothricin can be obtained in this manner in an enantiomeric purity of more than 94% ee.

The invention is described in more detail in the following examples; however, it is not restricted to the procedures illustrated as examples. In the examples percentage figures refer to weight, unless stated otherwise.

EXAMPLE 1

Bis-{3-[(4S)-3-benzyloxycarbonyl-5-oxo-1,3-oxazolidin-4-yl]propionyl} peroxide 15.9 ml (15.6 g, 0,197 mol) of pyridine are dissolved in 250 ml of diethyl ether and cooled to 0° C. and 14.5 g of hydrogen peroxide-urea complex (containing 35% hydrogen peroxide, 0.054 mol) are added. 30.7 g (0.098 mol) of 3-[(4S)-3-benzyloxycarbonyl-5-oxo-1,3-oxazolidin-4-yl]-propionyl chloride (prepared according to: Rec. Tray. Chim. 1975, 94, 182) are added in portions at 0–°5° C. The mixture is stirred for 5 hours with ice cooling, then 350 ml of ethyl acetate are added. The reaction mixture is washed once with 250 ml of 10% strength sulfuric acid, twice each time with 150 ml of saturated sodium hydrogen carbonate solution and once with water. The organic phase is separated off, dried over magnesium sulfate and concentrated under reduced pressure (put under high vacuum ) at temperatures below 30° C. The residue is purified by chromatography on silica gel (mobile phase: toluene/ethyl acetate). 13.9 g (48.5% of theory) of bis-{3-[(4S )-3-benzyloxycarbonyl-5-oxo-1,3-oxazolidin-4-yl]-propionyl} peroxide are obtained as a white solid. Analytical data: Peroxide content by iodometry=100%;

| | |
|---|---|
| $^1$HNMR(100MHz, CDCl$_3$) | 7.37(s, 10, C$_6$H$_5$), 5.54(d, 2, J=5Hz, NCH$_2$O), 5.23(d, 2, J=5Hz, NCH$_2$O), 5.19(s, 4, OC<u>H$_2$</u>—C$_6$H$_5$), 4.38 (t, 2, J=5.5Hz, CH(NCO)COO), 2.72–2.08(m, 8OC<u>CH$_2$CH$_2$</u>CH); |
| $^{13}$CNMR(75MHz, CDCl$_3$) | 171.240, 167.712, 153.074, 135.178, 128.735, 128.718, |

| | | |
|---|---|---|
| $C_{28}H_{28}N_2O_{12}$ (584.54): | 128.434, 77.877, 68.333, 53.815, 25.868, 25.504; | |
| | Calculated | C, 57.53; H, 4.83; N, 4.79 |
| | Found | C, 57.80; H, 4.90; N, 4.80 |

EXAMPLE 2

Bis-{3-[(4S)-3-benzyloxycarbonyl-5-oxo-1,3-oxazolidin-4-yl]acetyl} peroxide

Starting from 3-[(4S)-3-benzyloxycarbonyl-5-oxo-1,3-oxazolidin-4-yl]acetyl chloride (prepared according to: Tetrahedron 1986, 42, 6551), in a similar manner to Example 1, bis-{3-[(4S)-3-benzyloxycarbonyl-5-oxo-1,3-oxazolidin-4-yl]acetyl} peroxide is obtained in a yield of 56.8% of theory. Analytical data:

| | |
|---|---|
| $^1$HNMR(100MHz, CDCl$_3$) | 7.35(s, 10, C$_6$H$_5$), 5.45(d, 2, J=4.5Hz, NCH$_2$O), 5.28 (d, 2, J=4.5Hz, NCH$_2$O), 5.18(s, 4, OCH$_2$C$_6$H$_5$), 4.45 (t, 2, J=4.5Hz, CH(NCO)COO), 3.49–2.85(m, 4, OCCH$_2$CH). |

EXAMPLE 3

Bis-{3-[(4S)-B-toluenesulfonyl-5-oxo-1,3-oxazolidin-4-yl]propionyl} perioxide

Starting from 3-[(4S)-3-p-toluenesnlfonyl-5-oxo-1,3-oxazolidin-4-yl]propionyl chloride (prepared according to: Coll. .Czech. Chem. Comm. 1963, 28, 2941), bis-{3-[(4S)-3-toluenesulfonyl-5-oxo-1,3-oxazolidin-4-yl]propionyl} peroxide is obtained in a similar manner to Example 1 in 30.2% of the theoretical yield. Analytical data:

| | | |
|---|---|---|
| $^1$HNMR(100MHz, CDCl$_3$) | 7.71(d, 4, J=7.75Hz, C$_6$H$_5$), 7.35(d, 4, J=7.75Hz, C$_6$H$_5$), 5.49(d, 2, J=7.25Hz, NCH$_2$O), 5.24(d, 2, J=7.25 Hz, NCH$_2$O), 4.12 (m, 2, CH(NCO)COO), 2.92–2.57(m, 4, OCCH$_2$CH$_2$CH), 2.53–1.92(m, 4, OCCH$_2$CH$_2$CH), 2.43(s, 6, C$_6$H$_5$CH$_3$); | |
| $C_{26}H_{28}N_2O_{12}S_2$(624.65): | Calculated | C, 49.99; H, 4.52; N, 4.48 |
| | Found | C, 49.80; H, 4.80; N, 4.50. |

EXAMPLE 4

(4S)-3-Benzyloxycarbonyl-4-(2-chloroethyl)-1,3-oxazolidin-5-one 3.36 g (23.5mmol) of copper(I) oxide are suspended under an argon atmosphere in 280 ml of a 1:1 mixture of acetonitrile and acetic acid and are stirred for 10 min at room temperature. The resulting clear solution is heated to 50° C., and after dropwise addition of 4.89 g (23.5 mmol) of phosphorus(V) chloride, a solution of 13.60 g (23.3 mmol) of bis-{3-[(4S)-3-benzyloxycarbonyl-5-oxo-1,3-oxazolidin-4-yl]propionyl peroxide (obtained from Example 1) in 75 ml of acetonitrile is added. The mixture is stirred for a further 5.5 hours at 50° C. and 18 hours at room temperature, then the solvent is completely distilled off under reduced pressure (put under high vacuum) and the residue is taken up in 600 ml of ethyl acetate. The organic phase is washed once with 400 ml of 0.25 N hydrochloric acid and twice each time with 400 ml of water, dried over magnesium sulfate and evaporated to dryness. 12.7 g of a reddish oil are obtained, which according to the $^1$H-NMR spectrum is composed of 47% of (4S)-3-benzyloxycarbonyl-4-(2-chloroethyl)-1,3-oxazolidin-5-one and of 53% of 3-[(4S)-3-benzyloxycarbonyl-5-oxo-1,3-oxazolidin-4-yl]propionic acid. This oil is dissolved in 150 ml of toluene, the organic phase is washed once with 75 ml and once with 40 ml of saturated sodium hydrogen carbonate solution, dried over magnesium sulfate and concentrated. After chromatography on silica gel (mobile phase: toluene/ethyl acetate) 4.9 g (74.1% of theory) of (4S)-3-benzyloxycarbonyl-4-(2-chloroethyl)-1,3-oxazolidin-5-one are obtained as a white solid. Analytical data: Mp 75°–77° C.; $[\alpha]_D^{23}$=107.30° (c=0.481 CHCl$_3$);

| | | |
|---|---|---|
| $^1$HNMR(100MHz, CDCl$_3$) | 7.36(s, 5, C$_6$H$_5$), 5.54(d, 1, J=5Hz, NCH$_2$O), 5.27(dd, 1, J=5Hz, 2Hz, NCH$_2$O), 5.19(m, 2, OCH$_2$C$_6$H$_5$), 4.44 (td, 1, J=5.5Hz, 2Hz, CH(NCO)COO), 3.63(t, 2, J= 7Hz, ClCH$_2$CH$_2$), 2.53–2.25 (m, 2, ClCH$_2$CH$_2$CH); | |
| $^{13}$CNMR(75MHz, CDCl$_3$) | 171.671, 152.977, 135.231, 128.758, 128.408, 77.924, 68.230, 52.467, 39.685, 33.209; | |
| $C_{13}H_{14}NO_4Cl$(283.71): | Calculated | C, 55.04; H, 4.97; N, 4.94; Cl, 12.50 |
| | Found | C, 55.50; H, 5.10; N, 4.80. |

EXAMPLE 5

(4S)-3-Benzyloxycarbonyl-4-(2-bromoethyl)-1,3-oxazolidin-5-one 4.30 g (19.3 mmol) of copper(II) bromide are dissolved under an argon atmosphere in 320 ml of acetonitrile and heated to 50° C. and a solution of 20.43 g (35 mmol) of bis-{3-[(4S)-3-benzyloxycarbonyl-5-oxo-1,3-oxazolidin-4-yl]propionyl} peroxide (from Example 1) in 90 ml of acetonitrile is added dropwise. The mixture is stirred for 5.5 hours at 50° C. and 18 hours at room temperature. The solvent is distilled off completely under reduced pressure (put under high vacuum), the residue is taken up in 500 ml of ethyl acetate and is washed once with 500 ml of 0.25 N hydrochloric acid and twice each time with 50 ml of water. The organic phase is dried over magnesium sulfate and concentrated. 23.9 g of a semicrystalline solid are obtained, which according to the $^1$H-NMR spectrum is composed of 48% of (4S)-3-benzyloxycarbonyl-4-(2-bromoethyl)-1,3-oxazolidin-5-one and of 52% of 3-[(4S)-3-benzyloxycarbonyl-5-oxo-1,3-oxazolidin-4-yl]-propionic acid. This solid is dissolved in 350 ml of toluene and the solution is washed once with 300 ml and once with 200 ml of saturated sodium hydrogen carbonate solution, dried over magnesium .sulfate and concentrated in vacuo. After chromatography on silica gel (mobile phase: toluene/ethyl acetate), 10.3 g (89.6% of theory) of (4S)-3-benzyloxycarbonyl-4-(2-bromoethyl)-1,3-oxazolidin-5-one are obtained as a white solid.

Analytical data: Mp 85° C. [Literature value from J. Chem. Soc. Chem. Comm. 1984, 1298: 66.5° C.]; $[\alpha]_D^{23}$= 86° (c=0.929, CH$_3$OH) [Literature value from J. Chem. Soc. Chem. Comm. 1984, 1298: $[\alpha]_D$=54° (c=0.9, CH$_3$OH)];

| $^1$HNMR(100MHz, CDCl$_3$) | 7.37(s, 5, C$_6$H$_5$), 5.55 (d, 1, J=5Hz, NCH$_2$O), 5.26 (d, 1, J=5Hz, NCH$_2$O), 5.18 (s, 2, OC$\underline{H}_2$C$_6$H$_5$), 4.43 (t, 1, J=5.5Hz, CH(NCO)COO), 3.46 (t, 2, J=7Hz, BrC$\underline{H}_2$CH$_2$), 2.60–2.31(m, 2, BrCH$_2$C$\underline{H}_2$CH); |
|---|---|
| $^{13}$CNMR(75MHz, CDCl$_3$) | 171.466, 152.976, 135.190, 128.760, 128.453, 77.960, 68.262, 53.577, 33.568, 26.972; |
| C$_{13}$H$_{14}$NO$_4$Br(328.17): | Calculated    C, 47.58; H, 4.30; N, 4.27; Br, 24.35 |
| | Found    C, 47.80; H, 4.30; N, 4.10; Br, 25.20. |

Starting from bis-{3-[(4S)-3-benzyloxycarbonyl-5-oxo-1, 3-oxazolidin-4-yl]propionyl} peroxide (from Example 1), using various halogen donor/catalyst combinations, (4S)-benzyloxycarbonyl-4-(2-bromoethyl)-1,3-oxazolidin-5-one is obtained in the following yields (% of theory):

|  | Halogen donor | Catalyst | Solvent | Yield |
|---|---|---|---|---|
| Example 6 | CuBr$_2$ | CuBr$_2$ | Benzonitrile | 67.1% |
| Example 7 | CuBr | CuBr | Acetonitrile | 60.0% |
| Example 8 | PBr$_5$ | CU$_2$O | Acetonitrile/Acetic acid | 75.0% |
| Example 9 | Br$_2$ | CuBr$_2$ | Acetonitrile | 78.2% |

EXAMPLE 10

(4S)-3-Benzyloxycarbonyl-4-(2-iodoethyl)-1,3-oxazolidin-5-one 1.05 g (5.5mmol) of copper(I) iodide are dissolved under an argon atmosphere in 50 ml of acetonitrile and heated to 50° C. and a solution of 2.92 g (5 mmol) of bis-{3-[(4S)-3-benzyloxycarbonyl-5-oxo-1,3-oxazolidin-4-yl]-propionyl} peroxide (from Example 1) in 14 ml of acetonitrile is added dropwise. The mixture is ,stirred for 5.5 hours at 50° C. and 18 hours at room temperature. The solvent is completely distilled off under high vacuum, the residue is taken up in 100 ml of ethyl acetate and is washed once with 75 ml of 0.25 N hydrochloric acid and twice each time with 75 ml of water. The organic phase is dried over magnesium sulfate and concentrated. 3.1 g of a brown oil are obtained which, according to the $^1$H-NMR spectrum, is composed of 34% of (4S)-3-benzyloxycarbonyl-4-(2-iodoethyl)-1,3-oxazolidin-5-one and of 66% of 3-[(4S)-3-benzyloxycarbonyl-5-oxo-1,3-oxazolidin-4-yl]propionic acid. This oil is dissolved in 35 ml of toluene, washed once with 20 ml of saturated sodium hydrogen carbonate solution, dried over magnesium sulfate and concentrated in vacuo. Recrystallization from methanol leads to 0.95 g (50.6% of theory) of (4S)-3-benzyloxycarbonyl-4-(2-iodoethyl)-1,3-oxazolidin-5-one as a light brown solid.

Analytical data: Mp 79°–80° C. $[\alpha]_D^{23}=$ –80.5° (c=0.539, CHCl$_3$);

| $^1$HNMR(100MHz, CDCl$_3$) | 7.37(s, 5, C$_6$H$_5$), 5.55(d, 1, J=5Hz, NCH$_2$O), 5.24(d, 1, J=5 Hz, NCH$_2$O), 5.18 (s, 2, OC$\underline{H}_2$C$_6$H$_5$), 4.37(t, 1, J=5.5Hz, CH(NCO)COO), 3.21(t, 2, J=7 Hz, IC$\underline{H}_2$CH$_2$), 2.44 (q, 2, ICH$_2$C$\underline{H}_2$CH) |
|---|---|

EXAMPLE 11

(4S)-3-Benzyloxycarbonyl-4-(2-bromomethyl)-1,3-oxazolidin-5-one 1.40 g (6.23 mmol) of copper(II) bromide are dissolved under an argon atmosphere in 100 ml of acetonitrile and heated to 50° C. and a solution of 6.40 g (11.5 mmol) of bis-{3-[(4S)-3-benzyloxycarbonyl-5-oxo-1,3-oxazolidin-4-yl]acetyl} peroxide (from Example 2) in 35 ml of acetonitrile is added dropwise. The mixture is stirred for 4.5 hours at 50° C. and 18 hours at room temperature. The solvent is completely distilled off in high vacuum and the residue is taken up in 250 ml of ethyl acetate, washed once with 175 ml of 0.25 N hydrochloric acid and once with 175 ml of water. The organic phase is dried over magnesium sulfate and concentrated. 15.5 g of an oil are obtained which, according to the $^1$H-NMR spectrum, is a mixture of (4S)-3-benzyloxycarbonyl-4-(2-bromomethyl)-1,3-oxazolidin-5-one and 3-[(4S)-3-benzyloxycarbonyl-5-oxo-1,3-oxazolidin-4-yl]acetic acid. This oil is dissolved in 170 ml of toluene, washed once with 120 ml and once with 60 ml of saturated sodium hydrogen carbonate solution, dried over magnesium sulfate and concentrated in vacuo. 2.85 g (78.9% of theory) of (4S)-3-benzyloxycarbonyl-4-(2-bromomethyl)-1,3-oxazolidin-5-one are obtained as a light brown solid. Analytical data:

| $^1$HNMR(100MHz, DMSO-d$_6$) | 7.37(m, 5, C$_6$H$_5$), 5.44(d, 1, J=3.75Hz, NCH$_2$O), 5.32(d, 1, J=3.75Hz, NCH$_2$O), 5.20(s, 2, OC$\underline{H}_2$C$_6$H$_5$), 4.88 (m, 1, CH(NCO)COO), 3.91 (m, 2, BrC$\underline{H}_2$CH). |
|---|---|

EXAMPLE 12

(4S)-3-Benzyloxycarbonyl-4-{2-[ethoxy(methyl) phosphinyl]-ethyl}-1,3-oxazolidin-5-one 5.30 g (16.1 mmol) of (4S)-3-benzyloxycarbonyl-4-(2-bromomethyl)-1,3-oxazolidin-5-one (from Example 5) are mixed with 4.40 g (32.3 mmol) of diethyl methanephosphonite and the mixture is heated under argon for 6 hours at 120° C. The excess diethyl methanephosphonite is distilled off in high vacuum and the residue is purified by chromatography on silica gel (mobile phase: dichloromethane/acetonitrile). 4.64 g (81.1% of theory) of (4S)-3-benzyloxycarbonyl-4-{2-[ethoxy(methyl)phosphinyl]ethyl}-1,3-oxazolidin-5-one are obtained as a colorless oil. Analytical data: $[\alpha]_D^{23}=$ 91.61° (c=0.560, CHCl$_3$)

| $^1$HNMR(100MHz, CDCl$_3$) | 7.37(s, 5, C$_6$H$_5$), 5.53(d, 1, J=5Hz, NCH$_2$O), 5.23 (d, 1, J=5Hz, NCH$_2$O), 5.18(s, 2, OC$\underline{H}_2$C$_6$H$_5$), 4.37 (t, 1, J=5.5Hz, CH(NCO)COO), 4.01(quin d, 2, J=7Hz, 1.2Hz, POC$\underline{H}_2$CH$_3$), 2.47–1.55(m, 4, PC$\underline{H}_2$CH$_2$CH), 1.42 (d, 3, J=14Hz, H$_3$CP(O)), 1.28 (td, 3, J=7Hz, 1.2Hz, POCH$_2$C$\underline{H}_3$); |
|---|---|
| $^{31}$PNMR(121MHz, CDCl$_3$) | 52.863 |

The substance thus obtained is identical to the compound described in DE-A-3,817,956.

EXAMPLE 13

(4S)-3-Benzyloxycarbonyl-4-[2-(diethoxyphosphinyl) ethyl]-1,3-oxazolidin-5-one 3.28 g (10 mmol) of (4S)-3-benzyloxycarbonyl-4-(2-bromomethyl)-1,3-oxazolidin-5-one (from Example 5) are mixed with 3.39 g (20 mmol) of triethyl phosphite and the mixture is heated under argon for 18 hours at 120° C. The excess triethyl phosphite is distilled off under high vacuum and the residue is purified by chromatography on silica gel (mobile phase: dichloromethane/acetonitrile). 1.34 g (34.8% of theory) of (4S)-3-benzyloxycarbonyl-4-[2-(diethoxyphosphinyl) ethyl]-1,3-oxazolidin-5-one are obtained as a colorless oil. Analytical data: $[\alpha]_D^{23}=82.10°$ (c=0.402, CHCl$_3$)

| ¹HNMR(100MHz, CDCl₃) | 7.37(s, 5, C₆H₅), 5.53(d, 1, J=5Hz, NCH₂O), 5.23 (d, 1, J=5Hz, NCH₂O), 5.18(s, 2, OCH₂C₆H₅), 4.35 (t, 1, J=5.5Hz, CH(NCO)COO), 4.07(quin, 4, J=7Hz, POCH₂CH₃), 2.45–1.43(m, 4, PCH₂CH₂CH), 1,28(t, 3, J=7Hz, POCH₂CH₃); |
|---|---|
| ¹³CNMR(75MHz, CDCl₃) | 171.395, 152.906, 135.230, 128.706, 128.469, 128.351, 77.936, 68.146, 61.881, 61.797, 54.895, 54.636, 24.304, 24.071, 24.029, 21.923, 20.016, 16.422; |
| ³¹PNMR(121MHz, CDCl₃) | 29.853 |
| C₁₇H₂₄NO₇P(385.36): | Calculated C, 52.99; H, 6.28; N, 3.63; P, 8.04 |
| | Found C, 52.90; H, 6.40; N, 3.70; P, 7.70. |

EXAMPLE 14

L-homoalanin-4-yl(methyl)phosphinic acid hydrochloride (L-PTC-hydrochloride)

0.50 g (1.4 mmol) of (4S)-3-benzyloxycarbonyl-4-{2-[ethoxy (methyl)phosphinyl]ethyl}-1,3-oxazolidin-5-one (from Example 12) are, as described in DE-A-3,817,956, hydrolyzed by heating in 6 N hydrochloric acid. 0.25 g (82.1% of theory) of L-homoalanin-4-yl(methyl)phosphinic acid hydrochloride are obtained as a white solid having a melting point of Mp 202° C. (decomposition).

The enantiomeric excess, which was determined with the aid of an HPLC method (J. Chromatogr. 1986, 368, 413), is 94.6% ee.

EXAMPLE 15

L-2-Amino-4-phosphonobutyric acid hydrochloride 1.00 g (2.6 mmol) of (4S)-3-benzyloxycarbonyl-4-[2-diethoxyphosphinyl)ethyl]-1,3-oxazolidin-5-one (from Example 13) are, as described in DE-A-3,817,956, hydrolyzed by heating in 6 N hydrochloric acid. 0.57 g (100% of theory) of L-2-amino-4-phosphonobutyric acid hydrochloride are obtained as a light brown solid. Analytical data: $[\alpha]_D^{23}=17.3°$ (c=0.548, 1 N HCl);

| ¹HNMR(100MHz, D₂O) δ= | 4.12(t, 1, J=5.5Hz, CH(NH₂)COOH), 2.37–1.55(m, 4, PCH₂CH₂CH) |
|---|---|

What is claimed is:

1. An optically active compound of the formula I,

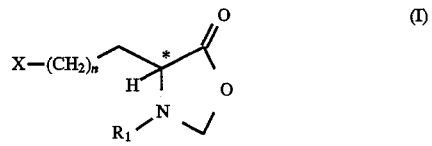

in which

R₁ is (C₁-C₆)alkyl which is unsubstituted or is substituted by one or more radicals selected from the group consisting of hydroxyl, (C₁-C₄)alkoxy, [(C₁-C₄)alkyl] carbonyl and [(C₁-C₄)alkoxy]carbonyl; or is (C₂-C₆) alkenyl, (C₂-C₄)alkynyl or a group of the formula R₂—CO— or R₃—SO₂—, R₂ is (C₁-C₁₁)alkyl, (C₆-C₁₃)aryl or substituted (C₆-C₁₃) aryl, (C₁-C₆)alkoxy, which is unsubstituted or substituted by one or more radicals, selected from the group consisting of (C₆-C₁₃)aryl and substituted (C₆-C₁₃) aryl, R₃ is (C₁-C₄)alkyl, phenyl or substituted phenyl, X is halogen, and n is zero or one, except for the compound of the formula I in which R₁=benzyloxycarbonyl, X=bromo or iodo and n=1.

2. A compound of the formula I as claimed in claim 1, wherein

R₁ is 1-hydroxy(C₁-C₆)alkyl, methanesulfonyl, benzenesulfonyl, o-, m- or p-toluenesulfonyl or a group of the formula R₂—CO—, R₂ is (C₁-C₁₁)alkyl, (C₆-C₁₂) aryl or substituted (C₆-C₁₂)aryl, (C₁-C₄) alkoxy, which is unsubstituted or is substituted by one or more radicals selected from the group consisting of phenyl and substituted phenyl, X is chlorine, bromine or iodine and is zero or one.

3. A compound as claimed in claim 1, wherein

R₁ is 1-hydroxy(C₁-C₄)alkyl, methanesulfonyl, benzenesulfonyl, p-toluenesulfonyl, methoxycarbonyl, ethoxycarbonyl, tertbutoxycarbonyl or benzyloxycarbonyl.

4. A compound as claimed in claim 1, which is an optically active (2S) compound of the formula I$_S$

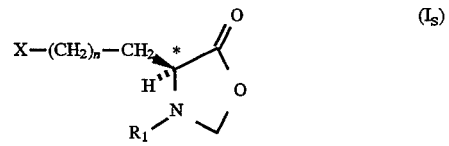

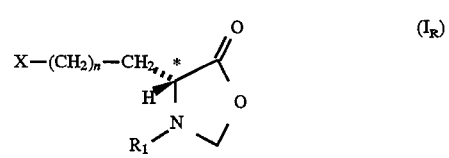

in which R₁, X and n are defined as in formula I as claimed in claim 1, or is a mixture of the isomers I$_S$ and I$_R$ having a content of more than 80% of the compound of the formula I$_S$.

* * * * *